United States Patent
Sharma et al.

(10) Patent No.: US 11,739,091 B2
(45) Date of Patent: Aug. 29, 2023

(54) **PROCESS FOR EXTRACTING AND PURIFYING RAUWOLSCINE FROM *RAUWOLFIA* PLANT**

(71) Applicants: Ashok Sharma, Punjab (IN); Rakesh Nag, Punjab (IN)

(72) Inventors: Ashok Sharma, Punjab (IN); Rakesh Nag, Punjab (IN)

( * ) Notice: Subject to any disclaimer, the term of this patent is extended or adjusted under 35 U.S.C. 154(b) by 109 days.

(21) Appl. No.: 17/073,327

(22) Filed: Oct. 17, 2020

(65) Prior Publication Data
US 2021/0115043 A1    Apr. 22, 2021

(51) Int. Cl.
*C07D 459/00*    (2006.01)
*C07D 471/14*    (2006.01)

(52) U.S. Cl.
CPC .................. *C07D 471/14* (2013.01)

(58) Field of Classification Search
CPC ... C07D 459/00; B01D 11/0288; A61K 36/00
USPC ..................................... 546/53, 50
See application file for complete search history.

(56) References Cited

U.S. PATENT DOCUMENTS 10,730,869 B2 *   8/2020   Tewari ................ C07D 459/00

FOREIGN PATENT DOCUMENTS

WO    WO-087778 A1 *   5/2018   ............. A61K 36/00

OTHER PUBLICATIONS

Pre Grant Opposition proceedings (filed by Pawan Goel on Aug. 13, 2021 with the Controller of Patents of the Indian Patent Office) directed toward the Indian parent application (201911037174, filed Oct. 20, 2019) of the present application.

* cited by examiner

*Primary Examiner* — Charanjit Aulakh

(57) ABSTRACT

The present invention relates to a process for extracting an alkaloid. Particularly, the present invention relates to a process for extracting Rauwolscine from plant parts of *Rauwolfia* genus. Specifically, the present invention relates to a process for extracting Rauwolscine with an enhanced purity i.e. >95%.

5 Claims, 4 Drawing Sheets

PROCESS FOR EXTRACTING AND PURIFYING RAUWOLSCINE FROM *RAUWOLFIA* PLANT

CROSS REFERENCE TO RELATED APPLICATION

This patent application claims the priority benefit of the INDIAN Non-provisional Patent Application No. 201911037174 filed on Oct. 20, 2019, disclosures of which is incorporated herein by reference in its entireties.

FIELD OF THE INVENTION

The present invention relates to a process for extracting an alkaloid. Particularly, the present invention relates to a process for extracting Rauwolscine from plant parts of *Rauwolfia* genus. Specifically, the present invention relates to a process for extracting Rauwolscine with an enhanced purity.

BACKGROUND OF THE INVENTION

Rauwolscine (17a-hydroxyyohimban-16a-carboxylic acid methyl ester) is an enantiomer of racemic compound yohimbine. Yohimbine is an indole alkaloid found in a variety of botanical sources such as the *Rauwolfia* root, is the principal alkaloid extracted from the bark of the *Pausinystalia yohimbe* tree. It has also been called quebrachine, aphrodine, corynine, and hydroaerogotocin. Rauwolscine is a potent selective $\alpha$-2 adrenoceptor (AR). The predominant use of Rauwolscine has been as a pharmacological tool to study the involvement of $\alpha$-2 ARs in the regulation of autonomic function and for the treatment of impotence in males. Rauwolscine is more selective on $\alpha$-2 receptors than $\alpha$-1 receptors, as much as 50 times more than the racemic compound. Since, the $\alpha$-2 receptors are in charge of fat storage and the $\alpha$-1 receptors have a role in adrenaline production, change in focus equals more targeted fat loss with less stimulant effects.

There are differences in the way Rauwolscine works on $\alpha$-2 receptors as well. It is more specific for alpha-2b and $\alpha$-2c receptors than for $\alpha$-2a receptors due to which in addition to stimulating weight loss. Rauwolscine increases motivation and focus and provides an energy boost, all with little or no side-effects. Effect of Rauwolscine on mood is similar to racemic compound; however, slightly more potent.

Rauwolscine is primarily extracted from the plant of *Rauwolfia* species. *Rauwolfia* is a genus of evergreen trees and shrubs in the family, Apocynaceae. *Rauwolfia* genus is mainly found in tropical regions of Africa, Asia, Latin America, and various oceanic islands. The best known species of *Rauwolfia* is *Rauwolfia caffra*, the South African quinine tree. *Rauwolfia* has 74 accepted species. *Rauwolfia serpentina*, commonly known as Indian Snakeroot or "Sarpagandha" contains a number of compounds which act as medicines/drugs e.g. including yohimbine, ajmaline, aricine, corynanthine, rauwolscine, reserpine, reserpiline, serpentinine etc. Another species, *Rauwolfia canescens* also contains a number of important phytochemicals. Different species of *Rauwolfia* differ in nature and quantities of phytochemicals present in them. In fact, a study has been reported in New England Journal of Medicine in which two species of *Rauwolfia* viz. *Rauwolfia serpentina* and *Rauwolfia canescens* were compared for their anti-hypertensive effects and reduced side effects. It was found that *Rauwolfia canescens* was superior to *Rauwolfia serpentina* in terms of improved therapeutic effects and reduced side-effects.

There are various processes available for extraction of Rauwolscine from *Rauwolfia* plants; however, the purity has been a big concern in these extraction processes. Many efforts have been carried out to invent extraction processes to obtain Rauwolscine of high purity; however, no process has been invented till date to achieve a purity lever of Rauwolscine approx. 95% or above.

SUMMARY OF THE INVENTION

The present invention provides a novel and improved process for extracting and purifying Rauwolscine.

In one aspect, the process of the present invention delivers Rauwolscine of purity level 95 to 98%.

In one another aspect, the process of the present invention is cost effective and easy.

In one another aspect, the process of the present invention eliminates the need of costly purification process, employing chromatographic techniques.

In one another aspect, the process of the present invention overall provides a simple and cost effective way to extract and purifying Rauwolscine.

DETAILED DESCRIPTION OF THE INVENTION

Figure 1:
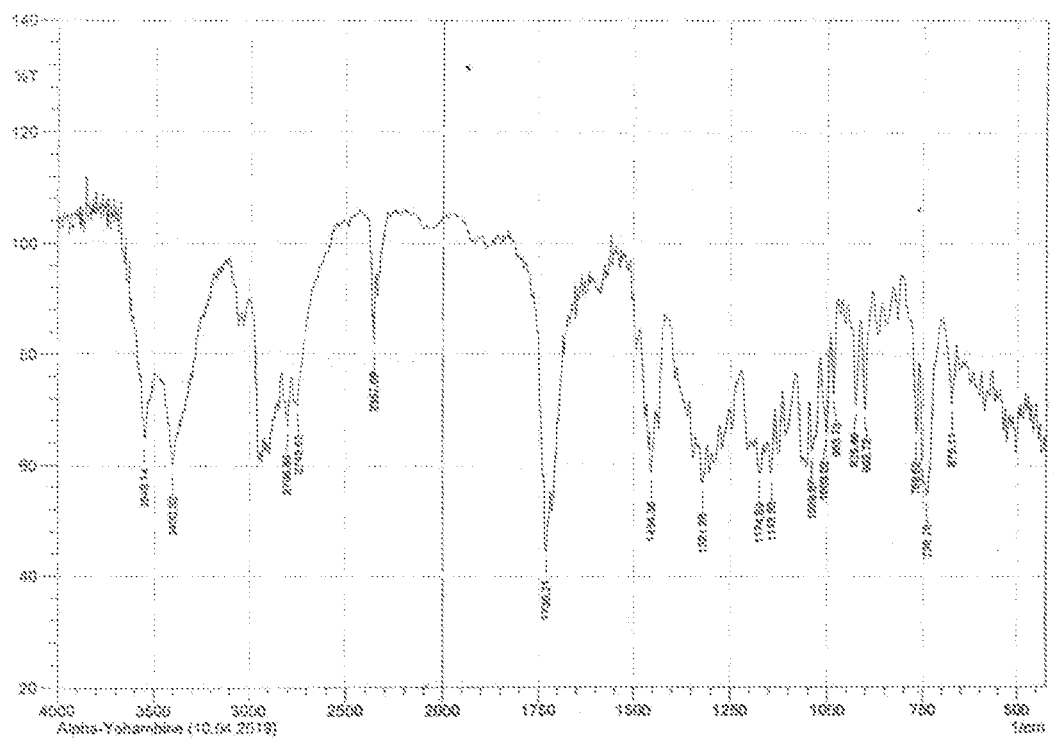
FIG. 1 is infrared (IR) spectroscopy of Rauwolscine extracted from the process of the present invention.
Figure 2:
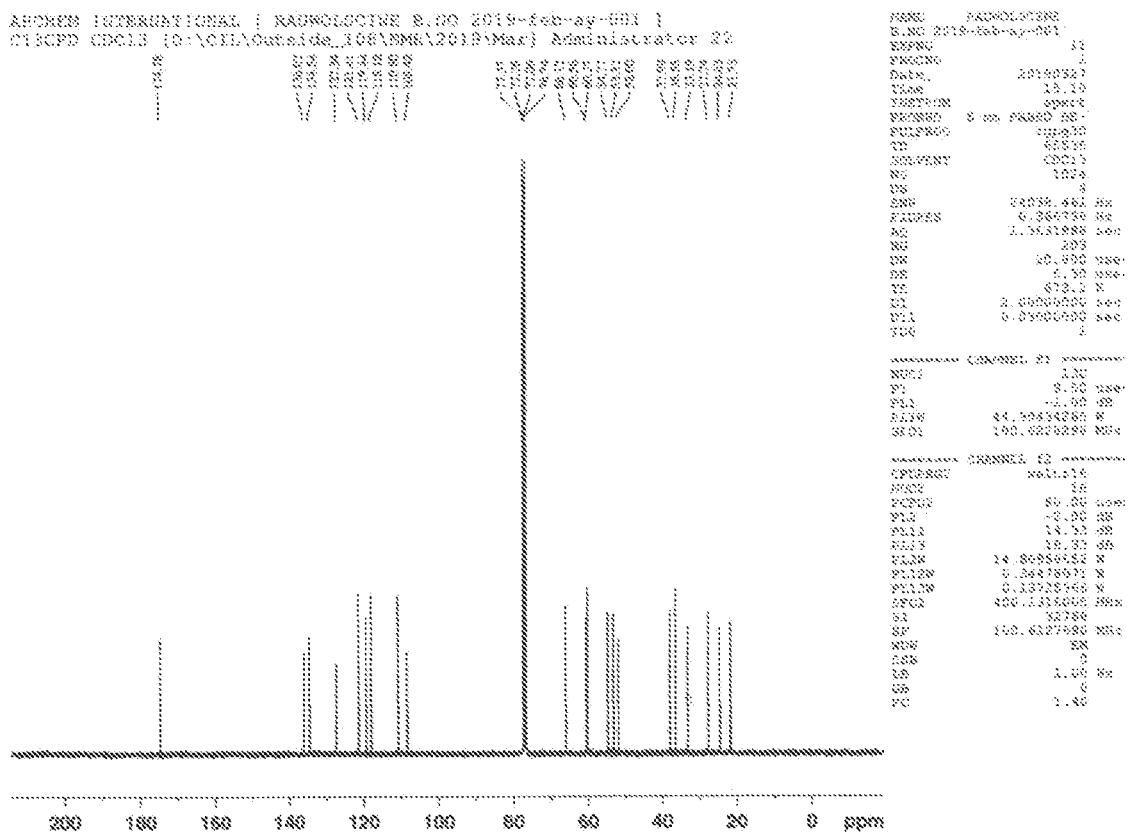
FIG. 2 is nuclear magnetic resonance (NMR) spectroscopy of Rauwolscine extracted from the process of the present invention.
Figure 3:
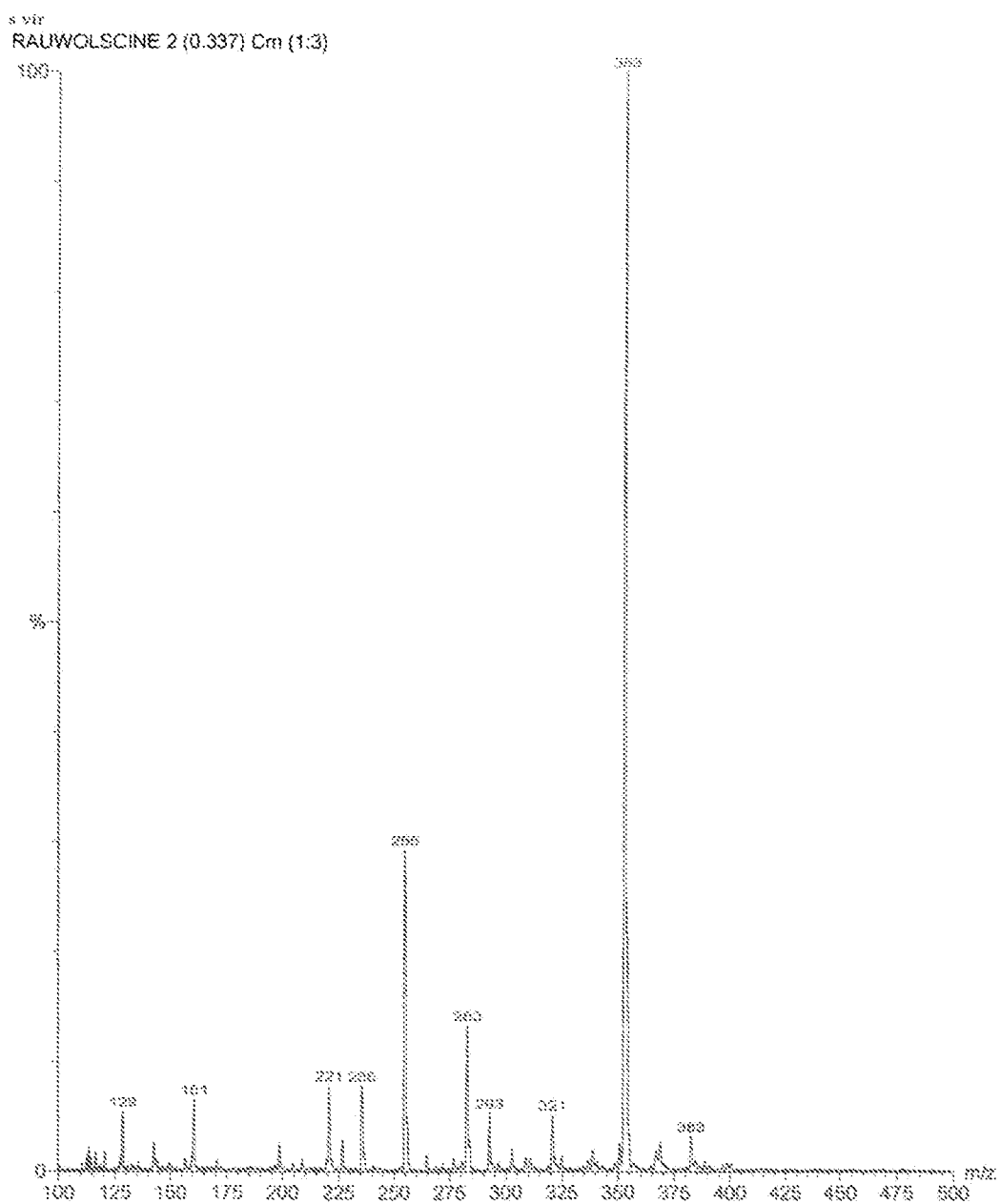
FIG. 3 is liquid chromatography mass spectroscopy (LCMS) of Rauwolscine extracted from the process of the present invention.
Figure 4:
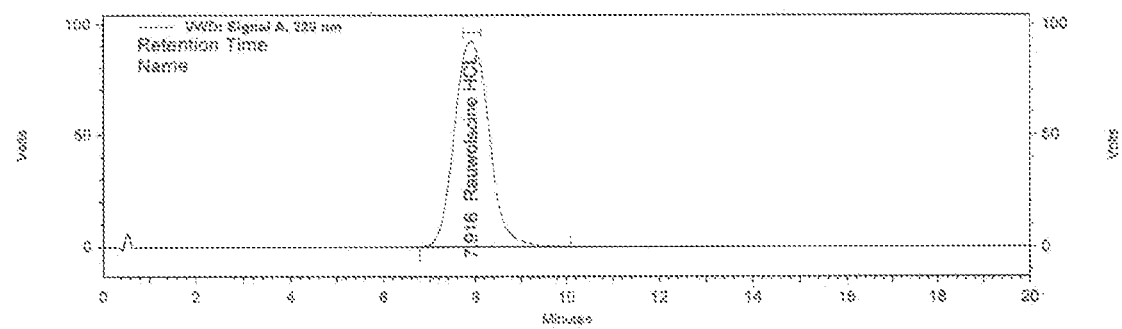
FIG. 4 is high performance liquid chromatography (HPLC) chromatogram of Rauwolscine extracted from the process of the present invention.

Various embodiments of the present disclosure will be described in detail with reference to the drawings, wherein like reference numerals represent like parts and assemblies throughout the several views. Reference to various embodiments does not limit the scope of the disclosure. Additionally, any examples set forth in this specification are not intended to be limiting and merely set forth some of the many possible embodiments for the present disclosure.

The present invention discloses a process for extracting an alkaloid. Particularly, a process for extracting Rauwolscine from plant parts of *Rauwolfia* genus is disclosed. Specifically, a process for extracting Rauwolscine with an enhanced purity is disclosed.

Definitions: It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "organic solvent" includes one or more such organic solvents and the like.

Unless defined otherwise, all technical, scientific or other terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "water-miscible solvent" refers to a solvent which is fully soluble in water at all pH; specifically, at a pH 7.0. The water-miscible solvent includes but not limited to polar solvents such as ethanol, methanol, acetone or any combination thereof.

The term "water-immiscible solvent" refers to a solvent which is insoluble in water. The water-immiscible solvent includes but not limited to ethyl acetate, hexane, chloroform, petroleum ether, dichloromethane and any combination thereof.

I. A Process for Extracting and Purifying Rauwolscine

The present invention discloses a novel and improved process for extracting and purifying Rauwolscine.

In one embodiment, the present invention discloses a process for extracting and purifying Rauwolscine, which delivers Rauwolscine of purity level 95 to 98%.

In one another embodiment, the present invention discloses a process for extracting and purifying Rauwolscine in cost effective and easy way.

In one another embodiment, the present invention discloses a process for extracting and purifying which eliminates the need of costly purification process, employing high cost chromatographic techniques.

In one another embodiment, the present invention discloses a process for extracting and purifying Rauwolscine, overall which provides a simple and cost effective way to extract and purify Rauwolscine.

The present invention discloses a process for extracting and purifying Rauwolscine; the process comprising the steps of: a) percolating dried *Rauwolfia* leaves for twice or thrice with a polar water-miscible organic solvent in a ratio 1:3 (*Rauwolfia* leaves: polar water-miscible organic solvent) at alkaline pH (8.0 to 9.0) at 40 to 50° C. for 2 to 4 hr with constant stirring; b) adding water, removing polar water-miscible organic solvent by drying under vacuum below 50° C., acidifying the aqueous extract with diluted hydrochloric acid (HCl) to adjust the pH around 3.0, filtering the acidified aqueous extract to remove oily residue, washing the filtrate with first non-polar organic solvents (twice or thrice) and then with second non-polar organic solvents (5 to 7 times washing); c) alkalizing (pH 8.5 to 8.8) the washed aqueous extract obtained in step (b), extracting the Rauwolscine in water-immiscible organic solvent, then precipitating the Rauwolscine by acidifying and cooling the resultant extract; d) dissolving the precipitate obtained in step (c) in hot water and removing the solvent by drying under reduced pressure, precipitating the Rauwolscine by alkalizing the resultant solution and washing the precipitate with water; e) dissolving the precipitate obtained in step (d) in hot methanol then treating it with activated charcoal and filtering it, acidifying the filtrate with diluted hydrochloric acid (HCl), cooling it at 5 to 15° C. and washing with methanol to obtain Rauwolscine hydrochloride; f) dissolving the precipitate obtained in step (e) in hot water, alkalizing the pH (8.0 to 9.0), cooling at 15 to 20° C., filtering and washing with water and then drying to obtain cream colored powder; and g) dissolving the cream colored power obtained in step (f) in hot methanol, treating it with activated charcoal and filtering it, treating the filtrate with aluminum oxide column to remove oily and colored impurities, acidifying the filtrate, cooling and drying for 4 to 6 hrs.

The polar water-miscible organic solvent is used in the step (a) is selected from ethanol, methanol or acetone. In one embodiment, the polar water-miscible organic solvent is used in the step (a) is ethanol. In one another embodiment, the polar water-miscible organic solvent is used in the step (a) is methanol. In one another embodiment, the polar water-miscible organic solvent is used in the step (a) is acetone.

In a specific embodiment, the polar water-miscible organic solvent is used in the step (a) is methanol.

The alkalizing agent used in the steps (a), (c) and (d) is ammonium hydroxide.

The acidifying agent used in the step (c) is concentrated solution of oxalic acid.

The water-immiscible organic solvent is selected from ethyl acetate or ether. In a preferred embodiment, the water-immiscible organic solvent is ethyl acetate.

The first non-polar organic solvent is selected from hexane or petroleum ether. In a preferred embodiment, the first non-polar organic solvent is hexane.

The second non-polar organic solvent is selected from chloroform or dichloromethane. In a preferred embodiment, the second non-polar organic solvent is chloroform.

Example-1

Extraction and Purification of Rauwolscine:

Procurement of *Rauwolfia* leaves and powdering: 1000 g leaves of *Rauwolfia canescens* were procured. The leaves were available commercially and procured from a vendor from Salem, Tamilnadu (India) area. The leaves were powdered. Extraction was then carried as described in the steps below:

Extraction of *Rauwolfia* Leaves:

Step-(a): The powdered leaves were then mixed with polar water-miscible organic solvent methanol at 40 to 50° C. in ratio of 1:3 i.e. 1 part powdered leaves and 3 parts solvent and made alkaline by addition of ammonia hydroxide solution to adjust pH 8.0 to 9.0 (alkaline). The powdered leaves were then allowed to percolate in the methanol for 2 to 4 hours in reactor with stirring followed by filtration. The filtrates/extracts were then transferred to another vessel. The remaining solid material was extracted twice or thrice with same solvent as above and the filtrates were pooled in the same vessel.

Step-(b): The pooled fractions were then combined, the solvent layers were concentrated under vacuum below 50° C. to get the syrup/viscous mass and added 50 L water to remove the traces of methanol under vacuum at 50° C. Added 300 L water to this syrup/viscous mass and adjusted its pH around 3.0 with dilute hydrochloric acid (HCl) at 40 to 50° C. Stopped the stirring and allowed to settle for 1 to 2 hrs. Then separated the aqueous acidic layer leaving behind the precipitated/sediment impurities. The same procedure of adding water, acidifying with dilute hydrochloric acid (HCl) and separating the aqueous acidic layer was repeated once more. The separated acidic water layers were collected and filtered through Hyflo® bed to remove oily residue. The filtrate was charged in reactor and washed with hexane 300 L (twice to thrice) and then with chloroform 200 L (5 to 7 times washing).

Step-(c): The above acidic aqueous layer was made slight alkaline (pH 8.5-8.8) and extracted with ethyl acetate thrice (300 L each time). The ethyl acetate layer was collected in the reactor and adjusted the pH 3-3.5 with saturated solution of oxalic acid in ethyl acetate, cooled to 10 to 15° C. The solution was maintained under stirring for 2 to 3 hrs, filtered and collected the Rauwolscine salt. Wet cake~weight=33-40 Kg; LOD~50 to 60%.

Step-(d): To prepare the free base wet cake (Rauwolscine salt) was dissolved in hot water 1:10 and removed the traces of solvent under reduced pressure at 50 to 60° C. Then the pH of the solution was adjusted to 8.5-9.0 with ammonium hydroxide. The solution was cooled to 15-20° C. The precipitated Rauwolscine was filtered, washed with water and dried for 15-20 hrs at 70 to 80° C. Obtained cream colored powder of Rauwolscine.

Step-(e): Rauwolscine base was dissolved in hot methanol (20 to 25 times of dry Rauwolscine powder). The solution was treated with activated charcoal and then filtered. The clear filtrate was made acidic (pH<2) with hydrochloric acid, then cooled to 5-15° C. for 3 to 4 hrs. The precipitated Rauwolscine was filtered, washed with methanol. The wet cake of Rauwolscine hydrochloride was collected.

Step-(f): Wet cake of rauwolscine hydrochloride was dissolved in hot water ~10 times. The solution was made just basic (pH 8.0-9.0) with ammonium hydroxide, cooled to 15-20° C. Then the precipitated Rauwolscine was filtered, washed with water and dried for 10 to 20 hrs. Rauwolscine hydrochloride was obtained as cream colored powder.

Step-(g): Above obtained cream colored powder was dissolved in hot methanol (20 to 25 times of dry Rauwolscine powder) followed by carbon treatment and filtration. The clear filtrate was passed through aluminum oxide column to remove oily and colored impurities. The clear filtrate was made acidic (pH<2) with hydrochloric acid, cooled to 5-15° C. for 3 to 4 hrs, filtered, slurry washed with methanol, filtered and dried under reduced pressure for 4-6 hrs. White colored Rauwolscine [α-yohimbine] hydrochloride was obtained.

Yield=3.5-4.5 kg
Assay/Potency=95-98%
Analytical data=IR, NMR (proton, C13), LCMS and HPLC

CHARACTERIZATION

Characterization of the purified Rauwolscine was done by Infrared Spectroscopy, nuclear Magnetic Resonance (NMR) spectroscopy, liquid chromatography mass spectroscopy (LCMS) and high performance liquid chromatography (HPLC) spectroscopy of Rauwolscine extracted from the process of the present invention.

We claim:

1. A process for extracting and purifying Rauwolscine; the process comprising the steps of:

a) percolating dried *Rauwolfia* leaves for twice or thrice with a water-miscible organic solvent in a ratio 1:3 (*Rauwolfia* leaves: water-miscible organic solvent) at alkaline pH (8.0 to 9.0) at 40 to 50° C. for 2 to 4 hr with constant stirring, with the water-miscible organic solvent being acetone, methanol, or ethanol;

b) then removing the water-miscible organic solvent by drying under vacuum below 50° C. and reducing the extract to a syrup, then adding water, then acidifying the aqueous extract syrup with diluted hydrochloric acid (HCl) to adjust the pH around 3.0, filtering the acidified aqueous extract to remove oily residue, washing the filtrate with first non-polar organic solvents (twice or thrice) and then with second non-polar organic solvents (5 to 7 times washing);

c) then alkalizing (pH 8.5 to 8.8) the washed aqueous extract obtained in step (b), extracting the Rauwolscine in the water-immiscible organic solvent, then precipitating the Rauwolscine by acidifying and cooling the resultant extract;

d) then dissolving the precipitate obtained in step (c) in hot water and removing the solvent by drying under reduced pressure, precipitating the Rauwolscine by alkalizing the resultant solution and washing the precipitate with water;

e) then dissolving the precipitate obtained in step (d) in hot methanol then treating it with activated charcoal and filtering it, acidifying the filtrate with diluted hydrochloric acid (HCl), cooling it at 5 to 15° C. and washing with methanol to obtain Rauwolscine hydrochloride;

f) then dissolving the precipitate obtained in step (e) in hot water, alkalizing the pH (8.0 to 9.0), cooling at 15 to 20° C., filtering and washing with water and then drying to obtain cream colored powder; and g) then dissolving the cream colored power obtained in step (f) in hot methanol, treating it with activated charcoal and filtering it, treating the filtrate with aluminum oxide column to remove oily and colored impurities, acidifying the filtrate, cooling and drying for 4 to 6 hrs.

2. The process of claim 1, wherein the alkalizing agent used in the steps (a), (c) and (d) is ammonium hydroxide.

3. The process of claim 1, wherein the acidifying agent used in the step (c) is concentrated solution of oxalic acid.

4. The process of claim 1, wherein the first non-polar organic solvent is hexane.

5. The process of claim 1, wherein the second non-polar organic solvent is chloroform.

* * * * *